United States Patent [19]

Hlasta

[11] Patent Number: 5,017,584

[45] Date of Patent: May 21, 1991

[54] ANTIDEPRESSANT 2-(4,5-DIHYDRO-1H-IMIDAZOLYL)-DIHYDRO-1H-INDOLES, -1,2,3,4-TETRAHYDROQUINOLINES AND -1H-INDOLES, AND METHODS OF USE THEREAS

[75] Inventor: Dennis J. Hlasta, Clifton Park, N.Y.

[73] Assignee: Sterling Drug Inc., New York, N.Y.

[21] Appl. No.: 802,409

[22] Filed: Nov. 27, 1985

Related U.S. Application Data

[63] Continuation-in-part of Ser. No. 684,406, Dec. 20, 1984, abandoned.

[51] Int. Cl.$^5$ .................. A61K 31/415; A61K 31/47; C07D 403/06; C07D 405/06
[52] U.S. Cl. .................... 514/314; 514/394; 514/395; 546/165; 546/167; 548/348; 548/465
[58] Field of Search .............. 546/165, 167; 548/465, 548/348; 514/314, 395, 394

[56] References Cited

U.S. PATENT DOCUMENTS 3,586,695  6/1971  Wysong ........................ 548/348
3,658,827  4/1972  Bezou ......................... 546/167

OTHER PUBLICATIONS

Chapleo et al., J. Med. Chem., 27, 570–576, (1984).
Chapleo et al., J. Med. Chem., 26, 823–831, (1983).
Wu et al., J. Med. Chem., 13, 975–978, (1970).
Kelarev et al., Khim. Geterotsikl. Soedin., 5, 645–650, (1980), [C.A. 93, 186079f, (1980)].
Kelarev et al., Izv. Vyssh. Uchebn. Zaved., Khim Tekhnol, 24, (11), 1354–1358, (1981), [C.A. 96, 68895h, (1982)].
Tominaga et al., Yakugaku Zasshi, 95, (9), 1073–1077, (1975), [C.A. 83, 206054t, (1975)].
Bitny-Szachto et al., Acta Polon. Pharm., 34, (5), 527–530, (1977).

*Primary Examiner*—David B. Springer
*Attorney, Agent, or Firm*—William G. Webb; Paul E. Dupont

[57] ABSTRACT

2-(4,5-Dihydro-1H-imidazol-2-yl)-2,3-dihydro-1H-indoles, 2-(4,5-dihydro-1H-imidazol-2-yl)-1,2,3,4-tetrahydroquinolines and 2-(4,5-dihydro-1H-imidazol-2-yl)-1H-indoles, useful as antidepressant agents, are prepared by reacting a respective lower-alkyl 2,3-dihydro-1H-indole-2-carboxylate 1,2,3,4-tetrahydroquinoline-2-carboxylate or 1H-indole-2-carboxylate derivative with ethylenediamine or an N-lower-alkylethylenediamine in the presence of a Lewis-type acid.

37 Claims, No Drawings

ANTIDEPRESSANT 2-(4,5-DIHYDRO-1H-IMIDAZOLYL)-DIHYDRO-1H-INDOLES, -1,2,3,4-TETRAHYDROQUINOLINES AND -1H-INDOLES, AND METHODS OF USE THEREAS

RELATED APPLICATIONS

This is a continuation-in-part of my prior, copending application Ser. No. 684,406, filed Dec. 20, 1984, now abandoned.

BACKGROUND OF THE INVENTION

This invention relates to 2-(4,5-dihydro-1H-imidazol-2-yl)-2,3-dihydro-1H-indoles, 2-(4,5-dihydro-1H-imidazol-2-yl)-1,2,3,4-tetrahydroquinolines and 2-(4,5-dihydro-1H-imidazol-2-yl)-1H-indoles, which are useful as antidepressant agents, and to a method of preparation thereof.

INFORMATION DISCLOSURE STATEMENT

Chapleo et al, J. Med. Chem. 27, 570–576 (1984) disclose certain 2-(4,5-dihydro-1H-imidazol-2-yl)benzo[b]-furans and 2-(4,5-dihydro-1H-imidazol-2-yl)benzo[b]-thiophenes having the formula:

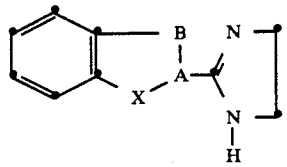

where X is O or S and the grouping A—B is CH—CH$_2$ or C=CH, which are stated to possess presynaptic $\alpha_2$-adrenoreceptor antagonist and postsynaptic $\alpha_1$-adrenoreceptor partial agonist properties.

Chapleo et al., J. Med. Chem. 26, 823–831 (1983) disclose a series of 2-(4,5-dihydro-1H-imidazol-2-yl)-1,4-benzodioxanes having the formula:

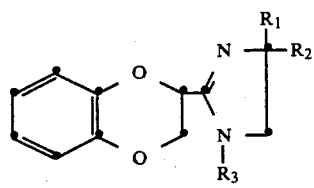

where R is hydrogen or a variety of substituents such as lower-alkyl, lower-alkoxy, hydroxy or halogen and R$_1$, R$_2$ and R$_3$ are each hydrogen or methyl. The compounds are stated to possess presynaptic $\alpha_2$-adrenoreceptor antagonist activity, and some species are said to possess $\alpha_1$-adrenoreceptor partial agonist properties.

Wu et al., J. Med. Chem. 13, 975–978 (1970) disclose 1-(4,5-dihydro-1H-imidazol-2-yl)-2,3-dihydro-1H-indole:

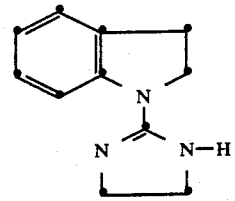

the maleate salt of which was tested for its analeptic activity by its antagonism of pentobarbital and of chloral hydrate, and found to be active and inactive, respectively. The compound was also tested for analgesic activity in the phenylquinone writing test and found to be active.

Species having the formula:

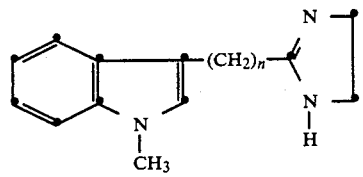

where n is 0 or 1 are disclosed by Kelarev et al., Khim Geterotsikl. Soedin., 5, 645–650 (1980) [C.A. 93, 186079f (1980)] and Kelarev et al., Izv. Vyssh. Uchebn. Zaved., Khim. Tekhnol., 24(11),1354–1358(1981)[C.A.96,68895h(1982)], but no utility for the compounds is disclosed.

The compound having the formula:

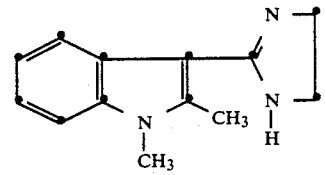

is disclosed by Tominaga et al., Yakugaku Zasshi, 95 (9), 1073–1077 (1975) [C.A. 83, 206054t (1975)], but no utility for the compound is disclosed.

Species having the formula:

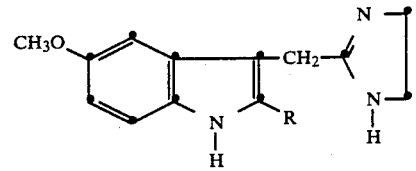

where R is hydrogen or methyl are disclosed by BitnySzachto et al., Acta Polon. Pharm. 34 (5), 527–530 (1977).

Compounds having the formula:

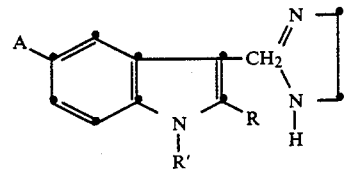

where A is hydrogen, bromine, chlorine, methyl or methoxy and R and R' are each hydrogen or methyl are disclosed by Wysong U.S. Pat. No. 3,586,695 (patented June 22, 1971), and are said to be useful as antidepressants.

SUMMARY OF THE INVENTION

In a product aspect, this invention relates to compounds having the formulas:

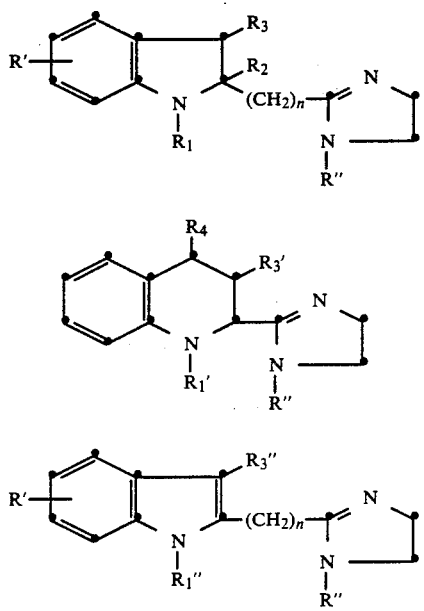

where, in compounds of formula I;
R' is hydrogen, halogen or benzyl;
R" is hydrogen or lower-alkyl;
$R_1$ is hydrogen, lower-alkyl, lower-alkenyl, lower-alkoxy-lower-alkyl, phenyl or phenyl-lower-alkyl;
$R_2$ is hydrogen, lower-alkyl, lower-alkenyl, lower-alkoxy-lower-alkyl, lower-alkylmercapto-lower-alkyl or di-lower-alkylamino-lower-alkyl;
$R_3$ is hydrogen, lower-alkyl or methylene; and
n is 0 or the integer 1;
in the compounds of formula II:
R" is hydrogen or lower-alkyl;
$R_1'$ is hydrogen or lower-alkyl;
$R_3'$ is hydrogen or lower-alkyl; and
$R_4$ is hydrogen or phenyl; and
in the compounds of formula III:
R' is hydrogen, halogen or benzyl;
R" is hydrogen or lower-alkyl;
$R_1''$ is lower-alkyl;
$R_3''$ is hydrogen or lower-alkoxy; and
n is 0 or the integer 1.

In a further composition aspect, the invention relates to a composition for treating depressed states in warm blooded animals which comprises an antidepressantly effective amount of a compound of formulas I, II or III together with a pharmaceutical excipient.

In a process aspect, the invention relates to a chemical process for preparing the compounds of formulas I, II or III which comprises reacting a respective compound of the formulas:

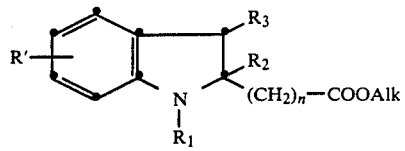

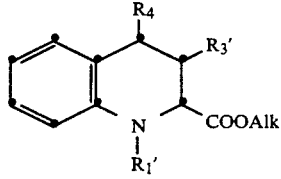

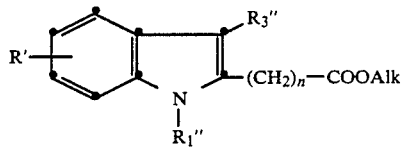

where R', $R_1$, $R_1'$, $R_1''$, $R_2$, $R_3$, $R_3'$, $R_3''$, $R_4$ and n have the meanings given above and Alk represents lower-alkyl, with ethylenediamine or an N-lower-alkylethylenediamine, in the presence of a Lewis-type acid.

In a further process aspect, the invention relates to a method for treating depressed states in warm blooded animals, which comprises administering a composition comprising an antidepressantly effective amount of a compound of formulas I, II or III.

DETAILED DESCRIPTION INCLUSIVE OF THE PREFERRED EMBODIMENTS

As used herein, the terms lower-alkyl and lower-alkoxy mean saturated, monovalent, aliphatic radicals, including branches chain radicals, of from one to four carbon atoms and thus represent methyl, ethyl, propyl, isopropyl, butyl, isobutyl, methoxy, ethoxy, propoxy, isopropoxy, butoxy and the like.

The compounds of formulas I, II and III are prepared by reacting an intermediate of formula IV, V or VI, respectively, with ethylenediamine or an N-lower-alkylethylenediamine. The reaction takes place at a temperature of a Lewis-type acid such as a tri-lower-alkyl aluminum, e.g. trimethylaluminum.

Alternatively, the compounds of formula II are prepared by reaction of a lower-alkyl 3-$R_3'$-4-$R_4$-quinoline-2-carboxylate of formula XIV with ethylenediamine under the same conditions described above, followed by catalytic reduction of the resulting 2-(4,5-dihydro-1H-imidazol-2-yl)-3-$R_3'$-4-$R_4$-quinoline of formula XV to produce the 2-(4,5-dihydro-1H-imidazol-2-yl)-3-$R_3'$-4-$R_4$-1,2,3,4-tetrahydroquinoline of formula II where R' and $R_1'$ are both hydrogen. If it is then desired to prepare the corresponding compounds of formula II where $R_1'$ is lower-alkyl, the compounds where $R_1'$ is hydrogen are reacted with di-t-butyl dicarbonate in the presence of an acid-acceptor, such as a tri-lower-alkylamine and in an inert organic solvent, such as tetrahydrofuran, dioxane, methylene dichloride or ethylene dichloride, to prepare the compounds of formula II' followed by reductive alkylation of the latter with a lower-alkanaldehyde and hydrolysis of the resulting $R_1'$-lower-alkyl substituted species to remove the t-butoxycarbonyl group and produce the compounds of formula II where R" is hydrogen. The reductive alkylation is carried out in conventional manner by using either chemical reducing agents, such as formic acid or an alkali metal cyanoborohydride, or with hydrogen over an appropriate catalyst, such as Raney nickel. Hydrolysis of the t-butoxycarbonyl group is effected by heating the ester with gaseous mineral acid in a lower-alkanol solvent. The overall process is represented by the reaction sequence:

is triethyl silane, and a preferred acid is trifluoroacetic acid.

Alternatively, the compounds of formula IV where $R_2$ is hydrogen and n is 0 are prepared by reduction of the compounds of formula VII with tin in the presence of a mineral acid, such as hydrochloric acid. The reaction is preferably carried out in an inert organic solvent, such as a lower-alkanol, and at a temperature from 0 to

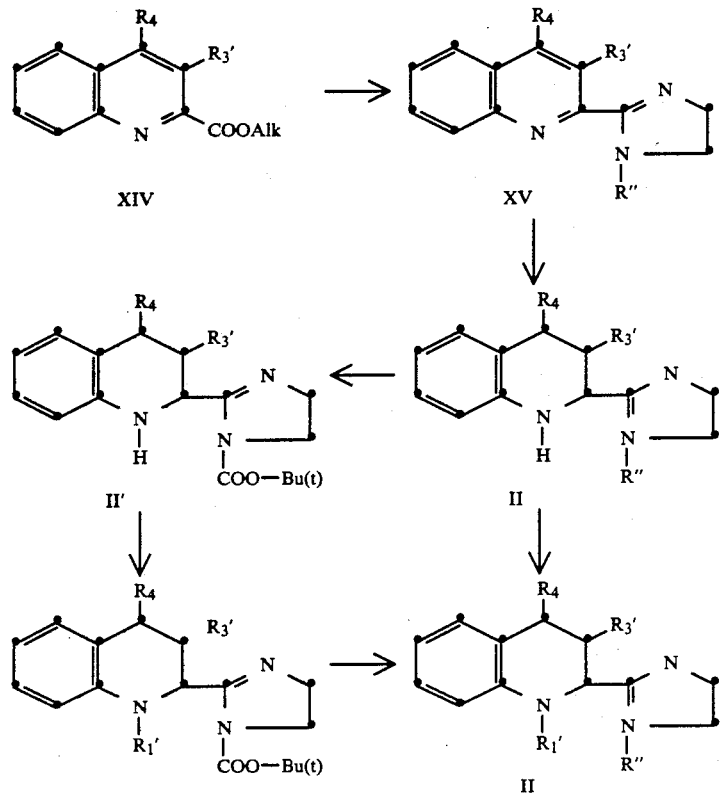

where R", $R_1'$, $R_3'$, $R_4$ and Alk have the meanings given above.

Alternatively, of course, the compounds of formula II where R" and $R_1'$ are both lower-alkyl can be prepared by reaction of the compounds of formula XIV directly with an N-lower-alkylethylenediamine, reduction of the resulting compound of formula XV to produce the compounds of formula II where $R_1'$ is hydrogen and R" is lower-alkyl and alkylation of the latter to produce the compounds of formula II where $R_1'$ is lower-alkyl. This approach thus obviates the need to proceed via the N-(t-butoxycarbonyl) derivative of formula II'.

The compounds of formula IV where $R_2$ is hydrogen and n is 0 are prepared by reduction of a compound of formula VII:

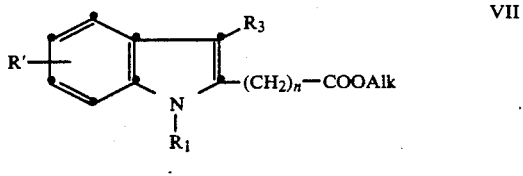

where R', $R_1$, $R_3$, Alk and n have the meanings given above, with a tri-lower-alkyl silane in the presence of a strong acid. The reaction takes place at a temperature in the range from 50 to 100° C. A preferred reducing agent

10° C.

The compounds of formula IV where n is 1 are advantageously prepared by reduction of the compounds of formula VII where n is 1 with an alkali metal cyanoborohydride in glacial acetic acid. The reaction takes place at a temperature in the range from 0 to 10° C.

The compounds of formula IV where $R_2$ is lower-alkyl, lower-alkenyl, lower-alkoxy-lower-alkyl, lower-alkylmercapto-lower-alkyl or di-lower-alkylamino-lower-alkyl and n is 0 are prepared by reaction of the corresponding compounds of formula IV where $R_2$ is hydrogen with a lower-alkyl halide, a lower-alkenyl halide, a lower-alkoxy-lower-alkyl halide, a lower-alkylmercapto-lower-alkyl halide or a di-lower-alkylamino-lower-alkyl halide in the presence of a strong base such as an alkali metal amide, an alkali metal hydride or an alkali metal di-lower-alkylamiiide, for example sodamide, sodium hydride or lithium diisopropyl amide. The reaction is carried out in an inert organic solvent such as tetrahydrofuran (THF) at a temperature around −78° C., i.e. in a dry ice/acetone bath.

Alternatively, the compounds of formula IV where $R_2$ is lower-alkyl containing from three to four carbon atoms can be prepared by reduction of the corresponding species where $R_2$ is lower-alkenyl with hydrogen over a suitable catalyst, for example palladium-on-charcoal, in an inert organic solvent, such as a lower-alkanol.

The compounds of formula IV where R₃ is methylene are prepared by reaction of an indoxyl derivative of formula XVI:

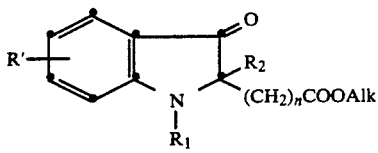

where R', R₁, R₂, Alk and n have the meanings given above, with a methyl triphenylphosphonium halide in the presence of a strong base, such as an alkali metal t-butoxide, in an organic solvent inert under the conditions of the reaction, such as THF, dioxane or diethyl ether.

The compounds of formula IV where R₁ is lower-alkyl, lower-alkenyl, lower-alkoxy-lower-alkyl or phenyl-lower-alkyl are advantageously prepared by N-alkylation of the corresponding indoles of formula VII above where R₁ is hydrogen, followed by reduction of the resulting product to the compounds of formula IV as described above. The alkylation is carried out by reaction of the indole with an appropriate alkylating agent in the presence of an acid-acceptor, such as an alkali metal carbonate or an alkali metal hydride, in an inert organic solvent, such as dimethylformamide (DMF).

The compounds of formula IV where R₁ is phenyl, as well as other species of formula IV where R₁ has the other meanings given above, are prepared by the Fischer indole synthesis in which an appropriate phenylhydrazone of formula VIII:

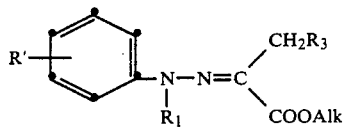

where R', R₁, R₃ and Alk have the meanings given above, or the corresponding carboxylic acid, is cyclized by heating in the presence of a strong acid, such as polyphosphoric acid or sulphuric acid, at a temperature in the range from 60 to 160° C., followed by reduction of the product of formula VII to the corresponding dihydro-1H-indole of formula IV as described above.

The compounds of formula VI where R₃'' is lower-alkoxy are prepared by reacting an appropriate indoxyl derivative of formula XVI':

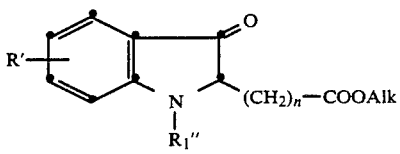

where R', R₁'', n and Alk have the meanings given above, with a tri-lower-alkyloxonium tetrafluoroborate in the presence of a strong base and in an inert organic solvent at a temperature from around −10° C. to 10° C. Suitable strong bases are the alkali metal lower-alkoxides, such as potassium t-butoxide, and suitable solvents are tetrahydrofuran, dioxane or diethyl ether.

The compounds of formula VII where R' and R₃ are hydrogen and where R₁ and Alk are lower-alkyl, which are prepared by the Fischer indole synthesis as described above, correspond, of course, to the compounds of formula VI which are precursors to the compounds of formula III as described above.

The compounds of formulas VI and VII where n is the integer 1 can also be prepared by acylation of an appropriate 2-unsubstituted-1H-indole with a di-lower-alkyl oxalate in the presence of a strong base, for example n-butyl lithium, in an inert organic solvent such as THF followed by catalytic reduction of the resulting lower-alkyl (1H-indol-2-yl)glyoxalate with hydrogen over a suitable catalyst, such as platinum oxide, in glacial acetic acid; and reaction of the resulting lower-alkyl (1H-indol-2-yl)glycolate with triphenylphosphine and iodine in an inert organic solvent such as benzene or toluene.

The compounds of formula IV where R' is benzyl are prepared by Friedel-Crafts acylation of the corresponding species where R' is hydrogen with a benzoyl halide in the presence of a Lewis-type acid such as aluminum chloride followed by reduction of the resulting benzoyl-substituted-2,3-dihydro-1H-indole with hydrogen over a catalyst, such as palladium-on-charcoal, in an inert organic solvent, such as a lower-alkanol. The compounds of formula IV thus prepared can be oxidized with a mild oxidizing agent, for example by passing a current of oxygen through a solution of the product in an appropriate organic solvent, to the corresponding compounds of formula VI where R' is benzyl.

The compounds of formula V, useful as precursors to the compounds of formula II, are prepared via the Friedlander quinoline synthesis which comprises reaction of an appropriate 2-R₄CO-aniline of formula IX with acetone in the presence of a strong acid. The resulting 4-R₄-2-methylquinoline of formula X is then brominated with bromine in glacial acetic acid in the presence of sodium acetate; the resulting 4-R₄-2-tribromomethylquinoline of formula XI is hydrolyzed with dilute sulphuric acid; the resulting 4-R₄-quinoline-2-carboxylic acid of formula XII is then reduced with sodium and butanol; the resulting 4-R₄-1,2,3,4-tetrahydroquinoline-2-carboxylic acid of formula XIII is then esterified; and, if appropriate, the resulting lower-alkyl 4-R₄-1,2,3,4-tetrahydroquinoline-2-carboxylate of formula V where R₁' is hydrogen is N-alkylated using conventional N-alkylation procedures, such as those described above in connection with the description of the N-alkylation of the compounds of formulas VI and VII. The overall process is illustrated by the following reaction sequence:

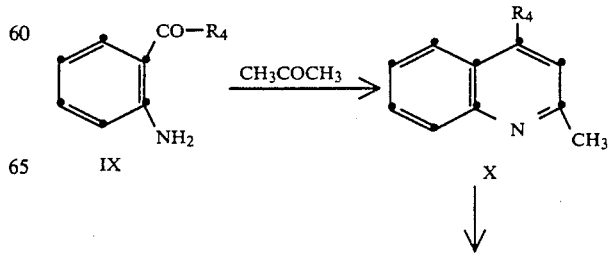

-continued

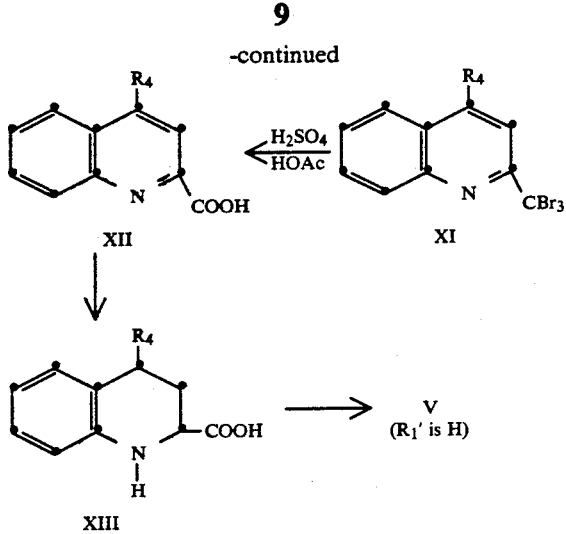

Due to the presence of basic amino groups in the compounds of formulas I, II and III, the free base forms represented by formulas I, II and III above react with organic and inorganic acids to form acid-addition salts. The acid-addition salt forms are prepared from any organic or inorganic acid. They are obtained in conventional fashion, for instance either by direct mixing of the base with acid or, when this is not appropriate, by dissolving either or both the base and the acid separately in water or an organic solvent and mixing the two solutions, or by dissolving both the base and the acid together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefor can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, maleic acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfuric acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, arsenic acid and the like.

All of the acid-addition salts are useful as sources of the free base forms which are generated by reaction of the salts with an inorganic base. It will thus be appreciated that if one or more of the characteristics such as solubility, molecular weight, physical appearance, toxicity, or the like of a given base or acid-addition salt thereof render that form unsuitable for the purpose at hand, it can be readily converted to another, more suitable form. For pharmaceutical purposes, acid-addition salts of relatively non-toxic pharmaceutically-acceptable acids, for example hydrochloric acid, lactic acid, tartaric acid, methanesulfonic acid, maleic acid and the like are, of course, employed.

The compounds of formulas I, II and III, and their acid-addition salts, have been found to possess $\alpha_2$-adrenergic antagonist properties indicative of anti-depressant activity.

The actual determination of the numerical pharmacological data for a particular compound of the invention is readily obtained according to test procedures, to be described in more detail below, by technicians versed in pharmacological test procedures without the need for any extensive experimentation.

In clinical practice, the compounds of formulas I, II and III, when used as antidepressants, are normally administered orally. Solid compositions for oral administration include compressed tablets, pills, powders and granules. In such solid compositions, at least one of the active compounds in admixed with at least one inert diluent such as starch, calcium carbonate, sucrose or lactose. These compositions can also contain additional substances other than inert diluents, for example, lubricating agents such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents, such compositions can also contain adjuvants, such as wetting and suspending agents, or sweetening, flavoring, perfuming and preserving agents. According to this invention, the compounds for oral administration also include capsules of adsorbable material, such as gelatin, containing the active component either with or without the addition of diluents or excipients.

The percentages of active components in such compositions may be varied so that a suitable dosage is obtained. The dosage administered to a particular patient is variable, depending upon the clinician's judgment using as criteria: the route of administration, the duration of treatment, the size and physical condition of the patients, the potency of the active component and the patient's response thereto. An effective dosage amount of the active component can thus only be determined by the clinician after a consideration of all criteria and utilizing his best judgment on the patient's behalf.

The structures of the compounds of the invention were established by the mode of synthesis, by elementary analyses and by ultraviolet, infrared and nuclear magnetic resonance spectra. The course of reactions was followed, and the homogeneity of the products was ascertained, by thin layer chromatography.

The manner and process of making and using the invention, and the best mode contemplated by the inventor of carrying out the invention, will now be described so as to enable any person skilled in the art to which it pertains to make and to use the same. The melting points are uncorrected.

PREPARATION OF INTERMEDIATES

A. The Intermediates of Formulas VI and VII

Preparation 1A

A solution of 232 g. (1.3 moles) of 4-chlorophenylhydrazine hydrochloride and 150 g. (1.29 moles) of ethyl pyruvate in 1050 ml. of absolute ethanol was heated under reflux for three and three quarter hours, stirred at ambient temperature for about twelve hours and then cooled in a refrigerator. The solid which separated was collected and dried to give 99 g. (31.5%) of the expected 4-chlorophenylhydrazone of ethyl pyruvate.

The latter (93 g., 0.39 mole) was added in small portions with stirring to 300 g. of polyphosphoric acid at 120° C. at such a rate that the reaction temperature was maintained at 120–150° C. without external heating. When addition was complete, the mixture was stirred at 145° C. for ten minutes, then cooled to 60° C. and diluted cautiously with 700 ml. of water with stirring. The solids which separated were collected and recrystallized from ethanol to give 58.4 g. (67% based on the hydrazone) of ethyl 5-chloro-1H-indole-2-carboxylate, m.p. 164–166° C.

Preparations 1B–1F

Following a procedure similar to that described in Preparation 1A above using an appropriate R′-substituted-phenylhydrazine and an appropriate α-keto acid or ester, $R_3CH_2COCOOAlk$, the lower-alkyl indole -2-carboxylates of formula VII listed in Table 1 were prepared where, in each instance, n is 0 and Alk is $C_2H_5$. Yields, in each instance, are based on the hydrazones. Here and elsewhere in the tables which follow, the melting points (in 0° C.) and the solvent used to recrystallize the products are given in columns headed "m.p./Solv.". Yields are given in percent.

TABLE 1

| Prep. | R′ | $R_1$ | $R_3$ | Yield | m.p./Solv. |
|---|---|---|---|---|---|
| 1B | 5-F | H | H | 44 | — |
| 1C | 7-Cl | H | H | 70 | — |
| 1D | H | H | $CH_3$ | 33 | 131–133 |
| 1E | H | $C_6H_5$ | H | 33 | cyclohexane |
| 1F | 5,7-$Cl_2$ | H | H | 63 | 149.5–150 |

Preparation 2A

A mixture containing 58.0 g. (0.24 mole) of ethyl 5-chloroindole-2-carboxylate, 102.1 g. (0.74 mole) of potassium carbonate and 105 g. (0.74 mole) of methyl iodide in 450 ml. of dry DMF was heated on a steam bath for two hours and then stirred at ambient temperature for about twelve hours. The mixture was then poured into an ice and water mixture with stirring, and the solid which separated was collected and dried to give 58.4 g. of ethyl 5-chloro-1-methyl-1H-indole-2-carboxylate.

Preparations 2B–2N

Following a procedure similar to that described in Preparation 2A above using an appropriate lower-alkyl R′-substituted-3-$R_3$-indole-2-carboxylate of formulas VI or VII, where $R_1$ or $R_1''$ are H, and an appropriate alkylating agent, the lower-alkyl $R_1$-substituted -1H-indole-2-carboxylates of formulas VI or VII, where in each instance n is 0, listed in Table 2 were prepared. The anionic portion of the alkylating agent ($R_1$—X or $R_1''$—X) and the acid-acceptor are given in the column headed "$X^-$/Base". The solvent used to recrystallize the product, if solid, or the physical state of the product are given in the column headed "Solv./State".

TABLE 2

| Prep. | R′ | $R_1$ | $R_3$ | $X^-$/Base | Yield | Solv./State | m.p. |
|---|---|---|---|---|---|---|---|
| 2B | 5-F | $CH_3$ | H | $I^-$/$K_2CO_3$ | 50 | EtOH/$H_2O$ | 68–69 |
| 2C | H | n-$C_3H_7$ | H | $I^-$/NaH | 100 | oil | |
| 2D | 7-Cl | $CH_3$ | H | $I^-$/$K_2CO_3$ | 37 | oil | |
| 2E | H | n-$C_4H_9$ | H | $I^-$/NaH | 100 | oil (b.p. 108–109/0.075 mm.) | |
| 2F | H | $CH_2CH=CH_2$ | H | $Br^-$/NaH | 100 | oil | |
| 2G | H | $CH_3$ | $CH_3$ | $I^-$/$K_2CO_3$ | 87 | oil | |
| 2H | H | $CH_2CH_2OC_2H_5$ | H | $Br^-$/NaH | 90 | oil | |
| 2I | H | $C_6H_5CH_2CH_2$ | H | $Br^-$/NaH | 26 | — | 82–83.5 |
| 2J | 5,7-$Cl_2$ | $CH_3$ | H | $I^-$/$K_2CO_3$ | 46 | iso-PrOH | |
| 2K | H | $CH_3$ | H | $I^-$/$K_2CO_3$ | 100 | — | 59.5–61.5 |
| 2L | H | $C_2H_5$ | H | $I^-$/NaH | 100 | oil (b.p. 103–105/0.20 mm.) | |
| 2M | H | $C_6H_5CH_2$ | H | $Cl^-$/$K_2CO_3$ | 77 | pentane | 60–61 |
| 2N | H | $CH_3$ | H | $I^-$/$K_2CO_3$ | 95 | — | 93–95 |

Preparation 3A

To a solution of 15 g. (0.114 mole) of 1-methyl-1H-indole in 300 ml. of THF was added dropwise, with stirring at 0° C., 57 ml. of a 2.2 M solution of n-butyl lithium (0.125 mole) in hexane. The solution was then stirred at ambient temperature for two hours and then treated dropwise over a ten minute period with a solution of 53 g. (0.45 mole) of dimethyl oxalate in 700 ml. of THF while cooling with an ice/methanol bath. The solution was then stirred for two hours, quenched with saturated sodium sulfate, concentrated to dryness in vacuo and the residue diluted with water and extracted with diethyl ether. The combined organic extracts, after washing first with water and then with saturated brine, were dried with magnesium sulfate and evaporated to dryness to give 26 g. of methyl 1-methyl-1H-indole-2-glyoxalate as a yellow oil.

The latter (20 g., 0.61 mole) was dissolved in 250 ml. of glacial acetic oxide at ambient temperature and an initial hydrogen pressure of 50.5 p.s.i.g. When reduction was complete (in about fifteen hours), the catalyst was removed by filtration, washed first with glacial acetic acid and then with methanol, and the combined filtrate was taken to dryness to give 7.9 g. (31%) of methyl 1-methyl-1H-indole-2-glycolate as a yellow gum.

The latter (0.036 mole) dissolved in 50 ml. of benzene was added to a solution of 18.9 g. (0.077 mole) of triphenylphosphine and 9.1 g. (0.036 mole) of iodine in 200 ml. of benzene. The mixture was heated under reflux under a nitrogen atmosphere for fifteen hours and was then cooled and poured into a dilute solution of potassium carbonate. The resulting mixture was extracted with chloroform, and the extracts were dried with magnesium sulfate and concentrated to dryness to give a yellow solid which was extracted with diethyl ether. The ether extracts, on concentration to dryness, gave 10 g. of an orange oil which was subjected to prepartive HPLC on two silica gel columns and eluted with 6% ethyl acetate in hexane. The first five fractions, consisting of 5.4 liters, were discarded and the next two fractions, consisting of 2.5 liters, were combined and taken to dryness to give 4.4 g. (60%) of methyl α-(1-methyl-1H-indol-2-yl)acetate as a pale yellow oil.

Preparation 3B

To a stirred suspension of 19.1 g. (0.17 mole) of potassium t-butoxide in 800 ml. of THF was added 32 g. (0.15 mole) of ethyl 1-methylindoxyl-2-carboxylate with stirring at 0° C. under a nitrogen atmosphere. The mixture was stirred for one hour at 0° C. and then treated with 25.1 g. (0.17 mole) of trimethyloxonium tetrafluoroborate. The mixture was stirred an additional two hours at 0° C. and then at ambient temperature for two hours, poured onto ice and extracted with diethyl ether. The ether extracts were washed first with water, then with brine, dried and taken to dryness to give 36.4 g. of a dark red oil which was chromatographed on silica gel in 5% ethyl acetate/hexane. The first major product was collected to give 20.5 g. (87%) of ethyl 3-methoxy-1-methylindol-2-carboxylate as an oil.

B. The Intermediate of Formula V

Preparation 4A

A solution of 100 g. (0.51 mole) of 2-aminobenzophenone, 110 ml. of acetone (1.5 moles) and 25 ml. of concentrated sulfuric acid in 500 ml. of glacial acetic acid was heated under reflux for four hours, diluted with an additional 55 ml. of acetone and heated under reflux for an additional two hours. The mixture was then cooled and poured into a mixture of 750 ml. of concentrated ammonium hydroxide and 2 liters of ice water. The yellow gum which separated crystallized on scratching and standing, and the solid was collected by filtration, washed with water an dried to give 107.7 g. (96%) of 2-methyl-4-phenylquinoline.

The latter (0.49 mole), suspended in a solution containing 255 g. (3.0 moles) of sodium acetate in 600 ml. of glacial acetic acid, was treated at 75° C. with a solution of 75 ml. (1.47 moles) of bromine in 60 ml. of glacial acetic acid. When addition was complete, the mixture was heated on a steam bath for one hour at 95° C. and allowed to stand at ambient temperature for three days. The solid which separated was collected, washed with water and dried to give 204 g. (91%) of 4-phenyl-2-tribromomethylquinoline, m.p. 100–104° C.

The latter (20.0 g., 0.044 mole) in 150 ml. of 10% sulphuric acid was heated on an oil bath at 120° C. for twenty-four hours, treated with 150 ml. of glacial acetic acid, heated for an additional twenty hours at 140° C. and then cooled and poured into ice water. The pH of the mixture was adjusted to about 6 by the addition of concentrated ammonium hydroxide, and the solid which had separated was collected, washed with water and recrystallized from dilute ethanol to give 6.7 g. (61%) of 4-phenylquinoline-2-carboxylic acid, m.p. 200–203° C.

The latter (4.0 g., 0.016 mole) was suspended in 50 ml. of n-butanol, and the mixture was treated, over a thirty minute period with refluxing and stirring, with 3.7 g. (0.16 mole) of sodium balls. The mixture was then heated under reflux for an additional hour and a quarter, and the n-butanol was removed by steam distillation. The resulting mixture was cooled, acidified with 6N hydrochloric acid and concentrated to dryness in vacuo. The residue was extracted with hot ethyl alcohol, and the combined extracts were taken to dryness to give an orange foam. The latter was dissolved in 100 ml. of absolute ethanol, and the solution saturated with anhydrous hydrogen chloride and heated under reflux for five hours. Dilution of the mixture with ethyl acetate, washing with dilute aqueous potassium carbonate, then with water, then with saturated brine and drying with magnesium sulfate and evaporation of the organic solution to dryness afforded 4.5 g. of ethyl 4-phenyl-1,2,3,4-tetrahydroquinoline-2-carboxylate as an orange oil which crystallized on standing, m.p. 85–90° C.

Preparation 4B

Following a procedure similar to that described in Preparation 4A above, 10 g. (0.058 mole) of quinoline-2-carboxylic acid was reduced with 14 g. (0.061 mole) of sodium balls in 170 ml. of n-butanol, and the resulting 1,2,3,4-tetrahydroquinoline-2-carboxylic acid was esterified with ethanol in the presence of hydrogen chloride to give 8.0 g. (67%) of ethyl 1,2,3,4-tetrahydroquinoline-2-carboxylate.

Preparation 5

A solution of 4.5 g. (0.022 mole) of ethyl 1,2,3,4-tetrahydroquinoline-2-carboxylate and 50 ml. of 37% formaldehyde in 200 ml. of absolute ethanol was reduced over 0.5 g. of 10% palladium-on-charcoal in a Parr shaker at an initial hydrogen pressure of 50 p.s.i.g. When reduction was complete (in about two hours), the catalyst was removed by filtration, and the filtrate was taken to dryness in vacuo. The residue, on dissolving in diethyl ether, washing sequentially with water, dilute aqueous sodium bicarbonate, water again and then saturated brine and drying with magnesium sulfate and concentration of the organic solution to dryness, afforded 4.3 g. (81%) of ethyl 1-methyl-1,2,3,-4-tetrahydroquinoline-2-carboxylate as a pale yellow oil.

C. The Intermediate of Formula IV

Preparation 6A

Methyl 1-methyl-1H-indole-2-carboxylate (11.5 g., 0.061 mole) was dissolved in 125 ml. of trifluoroacetic acid, and the solution was chilled in an ice bath and treated with 19 ml. (0.12 mole) of triethylsilane added in one portion. The mixture was heated under reflux for four hours, allowed to stand at ambient temperature for about twelve hours and then poured into an ice/35% aqueous sodium hydroxide mixture with vigorous stirring. The resulting mixture was extracted with diethyl ether, and the combined extracts were washed twice with water, once with saturated brine and extracted with ice cold 12N hydrochloric acid. The acid extracts, after backwashing with diethyl ether, were poured into an ice/35% sodium hydroxide solution and the mixture extracted with diethyl ether. The combined organic extracts, after washing with water and saturated brine and then drying with magnesium sulfate and concentration to dryness, afforded 4.8 g. (41%) of methyl 1-methyl-2,3-dihydro-1H-indole-2-carboxylate as a yellow oil.

Preparations 6B–6P

Following a procedure similar to that described in Preparation 6A using an appropriate ethyl R'-substituted-3-$R_3$-indole-2-carboxylate of formula VI or formula VII, the following $R_1$-substituted compounds of formula IV listed in Table 3, where in each instance n is 0, $R_2$ is H and Alk is $C_2H_5$, were prepared.

TABLE 3

| Prep. | R' | $R_1$ | $R_3$ | Yield | Phys. State |
|---|---|---|---|---|---|
| 6B | H | $C_2H_5$ | H | 47 | pale yellow oil |
| 6C | H | $C_6H_5CH_2$ | H | 39 | yellow oil |
| 6D | H | $CH_3$ | H | 67 | colorless oil, b.p. 94–96/0.03 mm. |
| 6E | 5-Cl | $CH_3$ | H | 26 | brown oil |
| 6F | 5-F | $CH_3$ | H | 42 | brown oil |
| 6G | H | $C_3H_7$ | H | 55 | yellow oil |
| 6H | 7-Cl | $CH_3$ | H | 62 | oil |
| 6I | H | $C_4H_9$ | H | 28 | yellow oil |
| 6J | H | $CH_2CH=CH_2$ | H | 28 | brown oil |
| 6K | H | $CH_2CH_2OC_2H_5$ | H | 16 | yellow oil |
| 6L | H | $C_6H_5CH_2CH_2$ | H | 56 | orange oil |
| 6M | H | $C_6H_5$ | H | 47 | clear oil |
| 6N | H | $CH_3$ | $CH_3$ cis-trans mixture | 22 | oil |
| 6O | 5,7-$Cl_2$ | $CH_3$ | H | 19 | oil |

Preparation 7

To a solution of 5.7 g. (0.028 mole) of methylα-(1-methyl-1H-indol-2-yl)acetate in 140 ml. of glacial acid was added, over a ten minute period while cooling in an ice bath, 8.8 g. (0.14 mole) of sodium cyanoborohydride. When addition was complete, the mixture was stirred at ambient temperature for four and a half hours, then diluted with 500 ml. of ice water and poured into an ice/35% sodium hydroxide solution. The mixture was extracted with diethyl ether, and the combined organic extracts, after washing with water, were extracted with ice cold 12N hydrochloric acid. The acid extracts, after backwashing with diethyl ether, were basified with ice/35% aqueous sodium hydroxide. Extraction of the resulting mixture with diethyl ether and evaporation of the ether extracts to dryness afforded 1.3 g. of methyl α-(1-methyl-2,3-dihydro-1H-indol-2-yl)acetate as a yellow oil.

Preparation 8

A stream of hydrogen chloride gas was bubbled through a mixture containing 73 g. (0.39 mole) of ethyl 1H-indole-2-carboxylate in 700 ml. of absolute ethanol for one and a quarter hours while cooling to 0° C. with an ice bath. The mixture was then treated with 55.6 g. (0.47 mole) of granular tin, stirred at ambient temperature for about twelve hours and then poured into ice water. The mixture was basified with ammonium hydroxide, extracted with diethyl ether, and the combined extracts were washed with water and then extracted with ice cold hydrochloric acid. The acid extracts, on rendering basic with 35% aqueous sodium hydroxide, extraction with ether and isolation of the product from the ether extracts, afforded 47.4 g. (64%) of ethyl 2,3-dihydro-1H-indole-2-carboxylate as a pale yellow oil which crystallized on cooling.

Preparation 9A

To a solution of 9.0 ml. (0.064 mole) of diisopropylamine in 250 ml. of dry THF cooled to −78° C. with a dry ice/acetone bath and under a nitrogen atmosphere was added 28 ml. (0.059 mole) of 2.1 M solution of n-butyl lithium in hexane. The solution was stirred at −78° C. forty-five minutes, treated dropwise with stirring at −78° C. with a solution of 10.8 g. (0.053 mole) of ethyl 1-methyl-2,3-dihydro-1H-indole-2-carboxylate, stirred for an additional thirty minutes at −78° C., treated dropwise with stirring at −78° C. with a solution of 5.5 ml. (0.064 mole) of allyl bromide in 30 ml. of dry THF, stirred for an additional one and a half hours at −78° C. and then quenched by the addition of 30 ml. of saturated aqueous ammonium chloride. The mixture was diluted with water and extracted with diethyl ether, and the combined organic extracts were washed first with water, then with saturated brine and dried with magnesium sulfate and concentrated to dryness to give 13.7 g. of a yellow oil which was subjected to preparative HPLC on silica gel and eluted with 3% ethyl acetate in hexane. The first three fractions, consisting of 2.5 liters of eluate, were combined and concentrated to dryness to give 12.8 g. of ethyl 1-methyl-2-(2-propenyl)-2,3-dihydro-1H-indole-2-carboxylate as a yellow oil.

Preparation 9B–9E

Following a procedure similar to that described in Preparation 9A above, reacting an appropriate alkylating agent ($R_2$ halide) with ethyl 1-methyl-2,3-dihydro-1H-indole-2-carboxylate in the presence of lithium diisopropylamide in THF, the following ethyl 1-methyl-2-$R_2$-2,3-dihydro-1H-indole-2-carboxylate of formula IV, where in each instance R' and $R_3$ are hydrogen, $R_1$ is $CH_3$ and Alk is $C_2H_5$ and n is 0, were prepared. The alkylating agent was the iodide, in the case of Preparation 9C and the chloride in the case of Preparation 9D. All products were obtained as yellow oils.

TABLE 4

| Prep. | $R_2$ | Yield |
|---|---|---|
| 9B | $CH_3$ | 100 |
| 9C | $CH_2OCH_3$ | 64 |
| 9D | $CH_2SCH_3$ | 19 |
| 9E | $CH_2N(iso-C_3H_7)_2$ | 20 |

Preparation 9E was carried out by reaction of the ethyl 1-methyl-2,3-dihydro-1H-indole-2-carboxylate with N,N-dimethylmethyleneammonium iodide (Eschenmoser's salt) in the presence of lithium diisopropylamide, and under the mechanism of this particular reaction, the latter served to aminate a transient intermediate produced from Eschenmoser's salt to thus produce the diisopropylamino compound rather than the expected dimethylamino species.

Preparation 10

To a solution of 9.1 g. (0.068 mole) of aluminum chloride in 50 ml. of ethylene dichloride was added, dropwise under a nitrogen atmosphere, a solution of 4.5 ml. (0.039 mole) of benzoyl chloride in 25 ml. of ethylene dichloride. The mixture was stirred at ambient temperature for thirty minutes and then treated rapidly dropwise with a solution of 7.0 g. (0.034 mole) of ethyl 1-methyl-2,3-dihydro-1H-indole-2-carboxylate in 25 ml. of ethylene dichloride. The mixture was heated on a steam bath for six hours, then cooled and poured into an ice/water mixture and the mixture extracted with ethyl acetate. The combined organic extracts were washed sequentially with water, dilute brine, then saturated brine and dried over magnesium sulfate and taken to dryness to give a brown oil. The latter was subjected to preparative HPLC on silica gel and eluted with 15% ethyl acetate in hexane. The second fraction was taken to dryness to give 6.7 g. (44%) of ethyl 5-benzoyl-1-methyl-2,3-dihydro-1H-indole-2-carboxylate.

The latter (5.7 g., 0.018 mole) in 200 ml. of absolute ethanol was reduced with hydrogen over 0.5 g. of 10% palladium-on-charcoal in a Parr shaker at ambient temperature and at an initial hydrogen pressure of 50 p.s.i.g. When reduction was complete, the catalyst was removed by filtration, and the filtrate was taken to dryness to give a yellow oil which was chromatographed on silica gel in 10% ethyl acetate in hexane, the second and third fractions, consisting of 200 ml. of eluate, being collected and taken to dryness to give 2.8 g. (53%) of ethyl 5-benzyl-1-methyl-2,3-dihydro-1H-indole-2-carboxylate.

Preparation 11

To a solution of 19.6 g. (0.055 mole) of methyl triphenylphosphonium bromide in 210 ml. of THF was added 6.2 g. (0.055 mole) of potassium t-butoxide while cooking in an ice bath under a nitrogen atmosphere. The ice bath was then removed, the solution was stirred for twenty minutes and then treated dropwise over a period of ten minutes with a solution of ethyl 1,2-dimethylindoxyl-2-carboxylate in 50 ml. of THF. The mixture was then stirred at ambient temperature for four hours, quenched with water and the mixture extracted with diethyl ether. The combined organic extracts, on washing with water, then brine, then drying and taking to dryness, afforded 20.9 g. of a yellow oily solid which was purified by HPLC in 7% ethyl acetate/hexane on silica, the first major fraction being collected as product. There was thus obtained 7.54 g. (78%) of ethyl 1,2-dimethyl-3-methylene-2,3-dihydro-1H-indole-2-carboxylate, m.p. 34–37° C.

PREPARATION OF THE FINAL PRODUCTS

EXAMPLE 1A

To a solution of 81 ml. (0.15 mole) of trimethylaluminum in 150 ml. of toluene, in a one liter, three-necked flask equipped with a condenser, nitrogen inlet tube and an addition funnel, was added a solution of 10.6 ml. (0.15 mole) of ethylenediamine in 55 ml. of toluene while cooling to 0° C. in an ice/methanol bath. The mixture was stirred at 0° C. for twenty minutes, then at ambient temperature for fifty minutes, treated dropwise with a solution of 11 g. (0.05 mole) of ethyl 5-fluoro-1-methyl-2,3-dihydro-1H-indole-2-carboxylate in 35 ml. of toluene, heated under reflux for two hours and then stirred at ambient temperature for about twelve hours. The reaction mixture was then quenched by the addition of 30 ml. of methanol and 10 ml. of water added dropwise while cooling with an ice/water bath, stirred for ten minutes, then diluted with 100 ml. of chloroform and heated under reflux for one hour. The mixture was then cooled with an ice bath, treated with about 10 g. of magnesium sulfate with stirring, filtered, and the filter washed with water and chloroform. The chloroform layer was separated from the filtrate, washed with water, then with saturated brine, dried over magnesium sulfate and taken to dryness in vacuo to give 9.3 g. (85%) of 2-(4,5-dihydro-1H-imidazol-2-yl)-5-fluoro-2,3-dihydro-1-methyl-1H-indole as a light yellow solid. A separate sample, recrystallized from isopropyl acetate, afforded the compound as a white crystalline solid, m.p. 138–139° C.

The main product was dissolved in ethyl acetate and the solution treated with excess ethereal hydrogen chloride. The solid which separated after cooling was collected and dried to give 9.1 g. of the hydrochloride salt, m.p. 272–274° C.

EXAMPLE 1B–1AG

Following a procedure similar to that described in Example 1A above using an appropriate lower-alkyl R'-substituted-1-R$_1$-2-R$_2$-3-R$_3$-2,3-dihydro-1H-indole-2-carboxylate or 2-acetate of formula IV, or a lower-alkyl 1-R$_1$'-4-R$_4$-1,2,3,4-tetrahydroquinoline-2-carboxylate of formula V or a lower-alkyl 1-R$_1$''-1H-indole-2-carboxylate or 2-acetate of formula VI, the compounds of formulas I, II and III listed in Table 4 were prepared. The structural identity of each of the species, whether of formulas I, II or III, is indicated in the column headed "form.". Unless noted otherwise R'', R$_3$' and R$_3$'' in compounds of formulas I, II and III, respectively, are hydrogen.

TABLE 5

| Exam. | Form. | R' | R$_1$/R$_1$'/R$_1$'' | R$_2$ | R$_3$ | R$_4$ | n | Base/Salt | Yield | m.p. (°C.)/Solv. |
|---|---|---|---|---|---|---|---|---|---|---|
| 1B | I | H | CH$_3$ | H | H | — | 0 | HCl | 89 | 182–207/ethyl acetate-EtOH |
| 1C | I | H | C$_2$H$_5$ | H | H | — | 0 | HCl.H$_2$O | 93 | 95–99/ethyl acetate-EtOH |
| 1D | I | H | CH$_3$ | CH$_2$CH=CH$_2$ | H | — | 0 | HCl | 93 | 242–247/EtOH-ether |
| 1E | I | H | C$_6$H$_5$CH$_2$ | H | H | — | 0 | maleate | 30 | 143–145/ethyl acetate |
| 1F | I | H | CH$_3$ | CH$_3$ | H | — | 0 | maleate | 82 | 140.5–143.5/ethyl acetate-ether |
| 1G | I | H | CH$_3$ | H | H | — | 1 | HCl.¼H$_2$O | 60 | 201–204/EtOH |
| 1H | I | 5-Cl | CH$_3$ | H | H | — | 0 | HCl | 95 | 250–253/EtOH-ether |
| 1I | I | H | CH$_3$ | n-C$_3$H$_7$ | H | — | 0 | HCl | 76 | 241–245/EtOH-ethyl acetate |
| 1J | I | H | n-C$_3$H$_7$ | H | H | — | 0 | maleate | 53 | 113–115/ethyl acetate |
| 1K | I | 7-Cl | CH$_3$ | H | H | — | 0 | maleate | 28 | 135.5–137/ethyl acetate |
| 1L | I | H | n-C$_4$H$_9$ | H | H | — | 0 | tosylate | 19 | 135–137/isopropanol-ether |
| 1M | I | H | CH$_2$CH=CH$_2$ | H | H | — | 0 | tosylate | 57 | 147–149/isopropanol |
| 1N | I | H | C$_2$H$_5$OCH$_2$CH$_2$ | H | H | — | 0 | HCl | 59 | 178–179/EtOH-ether |
| 1O | I | H | H | H | H | — | 0 | base | 10 | 140–148/ethyl acetate |
| 1P | I | 5-C$_6$H$_5$CH$_2$ | CH$_3$ | H | H | — | 0 | maleate | 69 | 152–155/EtOH-ether |
| 1Q | I | H | C$_6$H$_5$CH$_2$CH$_2$ | H | H | — | 0 | base | 88 | 134.5–136 |
| 1R | I | H | C$_6$H$_5$ | H | H | — | 0 | maleate | 66 | 176.5–178/ethyl acetate |

TABLE 5-continued

| Exam. | Form. | R' | R₁/R₁'/R₁" | R₂ | R₃ | R₄ | n | Base/Salt | Yield | m.p. (°C.)/Solv. |
|---|---|---|---|---|---|---|---|---|---|---|
| 1S | I | 5,7-Cl₂ | CH₃ | H | H | — | 0 | tosylate | 57 | 189–191/ethyl acetate |
| 1T | I | H | CH₃ | H | CH₃ (trans)$^{(a)}$ | — | 0 | tosylate | 27 | 163–165/isopropanol-ether |
| 1U | II | — | H | — | — | H | — | HCl.½H₂O | 57 | 210–230/EtOH-ethyl acetate |
| 1V | II | — | CH₃ | — | — | H | — | HCl | 19 | 237–252/EtOH-ether |
| 1W | II | — | H | — | — | C₆H₅ | — | base | 57 | 126–131/ethyl acetate-hexane |
| 1X | III | — | CH₃ | — | — | — | 1 | base | 60 | 122–134/ethyl acetate-cyclohexane |
| 1Y | III | — | CH₃ | — | — | — | 0 | HCl | 36 | 260–280/EtOH-ethyl acetate |
| 1Z | I | H | CH₃ | H | CH₃ (cis)$^{(a)}$ | — | 0 | tosylate | 10 | 173.5–174.5/isopropanol-ether. |
| 1AA | I | H | CH₃ | CH₂OCH₃ | H | — | 0 | HCl | 87 | 245–251/EtOH-ether |
| 1AB | I | H | CH₃ | CH₂SCH₃ | H | — | 0 | tosylate | 28 | 193–194/EtOAc |
| 1AC | I | H | CH₃ | CH₂N(iso-C₃H₇)₂ | H | — | 0 | maleate | 72 | 137.5–139/isopropanol-ether |
| 1AD | I$^{(b)}$ | H | CH₃ | H | CH₃ | — | 0 | tosylate | 9 | 130–131/CH₃CN-ether |
| 1AE | I | H | CH₃ | H | CH₃ | — | 1 | tosylate | 17 | 128–133/EtOH-ether |
| 1AF | I | H | CH₃ | CH₃ | =CH₂ | — | 0 | tosylate | 45 | 196.5–198.5/EtOH-ethyl acetate |
| 1AG | III | — | CH₃ | — | CH₃O$^{(c)}$ | — | 0 | maleate | 49 | 121–124/EtOH-ether |

$^{(a)}$The cis-trans isomer mixture, prepared from starting material of Prep. 6P, was column chromatographed on silica gel and gradient eluted with 1% triethylamine and 4% methanol in ethyl acetate to 3% triethylamine and 7% methanol in ethyl acetate. The trans isomer was eluted first from the column followed by the cis-isomer. The 1:1 diastereomeric mixture of the cis:trans tosylate isomers has m.p. 139.5–142° C.
$^{(b)}$R" is C₂H₅. Prepared by reaction of N-ethylethylenediamine with starting material of formula IV.
$^{(c)}$R₃" is CH₃O.

EXAMPLE 2

Methyl 3-methylquinoline-2-carboxylate (15.6 g., 0.078 mole) was reacted with 17.4 ml. (0.260 mole) of ethylenediamine in the presence of 0.232 mole of trimethyl aluminum in 230 ml. of toluene using the procedure described above in Example 1A. There was thus obtained 18.3 g. of N-(2-aminoethyl)-3-methylquinoline-2-carboxamide which was cyclized in 600 ml. of xylene in the presence of 0.156 mole of trimethyl aluminum. There was thus obtained 14.4 g. of 2-(4,5-dihydro-1H-imidazol-2-yl)-3-methylquinoline as a yellow solid which was converted to the hydrochloride salt to give 16.6 g. (86%) as a yellow powder, m.p.>300° C.

The latter (0.066 mole) was dissolved in a solution of 150 ml. of water and 150 ml of ethanol and reduced with hydrogen at room temperature in a Parr shaker at 50 p.s.i.g. over 0.6 g. of platinum oxide. When reduction was complete, the reaction mixture was filtered and concentrated to give 2-(4,5-dihydro-1H-imidazol-2-yl)-3-methyl-1,2,3,4-tetrahydroquinoline as a light yellow paste.

The latter (approximately 0.066 mole) was dissolved in a solution of 100 ml. of water and 100 ml. of dioxane, the solution was treated at 0° C. with 12 ml. (0.086 mole) of triethylamine, and the solution was then treated with a solution of 17.3 g. (0.079 mole) of di-t-butyl dicarbonate in 80 ml. of dioxane. The solution was stirred at ambient temperature for two and a half hours, then diluted with water and extracted with ethyl acetate. The combined organic extracts, on drying and concentration to dryness, afforded 21.4 g. of product as a pale yellow oil which was purified by HPLC, the product being eluted with 25% ethyl acetate/hexane. The first major product to be eluted was collected and recrystallized from hexane to give 6.54 g. (31%) of 2-(1-carbo-t-butoxy-4,5-dihydro-1H-imidazol-2-yl)-3-methyl-1,2,3,4-tetrahydroquinoline, m.p. 138–139° C.

The latter (4.72 g., 0.015 mole), mixed with 1.51 g. (0.024 mole) of sodium cyanoborohydride, 6 ml. of 37% formaldehyde and 100 ml. of acetonitrile, was treated with 1.2 ml. of acetic acid and then stirred at room temperature for two and a half hours. An additional 0.6 ml. of acetic acid was added, the mixture was stirred for an additional thirty minutes and then diluted with ethyl acetate and the mixture washed twice with brine, dried and taken to dryness to give 5.37 g. of a yellow solid which was purified by HPLC on silica gel, the product being taken off as the first major fraction. There was thus obtained 3.83 g. (77%) of 2-(1-carbo-t-butoxy-4,5-dihydro-1H-imidazol-2-yl)-1,3-dimethyl-1,2,3,4-tetrahydroquinoline, m.p. 123.5–128.5° C.

The latter (2.94 g., 0.089 mole) was dissolved in 50 ml. of a 5.44 N solution of ethanolic hydrogen chloride and the mixture heated under reflux for two hours and forty-five minutes. The mixture was taken to dryness, the residual green oil was dissolved in water and the solution poured into an ice/5% sodium hydroxide solution. Extraction of the mixture with chloroform and recovery of the organic soluble material from the organic layer by washing with water and evaporation to dryness afforded 2.45 g. of crystals which were dissolved in ethyl acetate. Treatment of the solution with 1.24 g. of maleic acid and collection and drying of the crystals which separated afforded 2.55 g. (83%) of 2-(4,5-dihydro-1H-imidazol-2-yl)-1,3-dimethyl-1,2,3,4-tetrahydroquinoline maleate, m.p. 142–144° C.

BIOLOGICAL TEST RESULTS

The $\alpha_2$-adrenergic antagonist activity of the compounds of the invention was determined by three screening methods, described as follows:

Tritiated Clonidine Receptor Binding Assay

Affinity is determined by assessing the ability of compounds to inhibit binding of $^3$H-clonidine (an $\alpha_2$-adrenergic agonist) to membranes of rat brain. Homogenates of rat cerebral cortex are incubated with 0.4 nM $^3$H-clonidine which binds to the $\alpha_2$-adrenergic binding sites (receptor) present on the membranes of the homogenate. Compounds that bind to the $\alpha_2$-adrenergic receptor, when added to the incubation mixture, will inhibit $^3$H-clonidine from binding to its site, thereby diminishing the amount of bound radioactivity. The amount of $^3$H-clonidine still bound is quantitated by liquid scintillation spectrometry. The results are expressed either in terms of percent inhibition at the concentration of antagonist used or as $K_i$ values. $K_i$ is a measure of the apparent affinity of the test substances for the $\alpha_2$-adrenergic binding site, as determined by the method of Cheng and Prusoff, Biochemical Pharmacology 22, 3099 (1973).

Vas Deferens Assay

Activity is determined by assessing the ability of compounds to antagonize the inhibition of twitch height induced by clonidine in the isolated, electrically stimulated rat vas deferens. Clonidine (10 nM) is added to the tissue bath and percentage inhibition of twitch height is calculated. The tissue is then rinsed to remove clonidine and, when the twitch height has returned to normal, the test compound is added. The ability of clonidine to inhibit twitch height is then again determined, and the clonidine-induced inhibition in the presence of the test compound is used to calculate percent antagonism of clonidine. Results are expressed either in terms of percent inhibition at the concentration of antagonist used or as $pA_2$ values, determined by the Schild method; cf. Tallarida and Murray, Manual of Pharmacologic Calculations, pp. 29-32 (Springer-Verlag, 1981). The $pA_2$ value is the negative logarithms of the concentration of antagonist required to cause a two-fold shift in the dose response curve to clonidine-induced inhibition of twitch height.

In Vivo Antagonism of Clonidine-Induced Anti-Nociception

The intraperitoneal administration of phenyl-p-quinone (PPQ) to mice elicits a nociceptive response which consists of abdominal writhing and extension of the hind limbs. This writhing response is prevented in mice pretreated with clonidine. When an $\alpha_2$-adrenergic antagonist is given prior to clonidine, the mice display the writhing response when PPQ is administered. To groups of thirty male mice for each experiment, the test compound dissolved in 0.9% sodium chloride was administered either subcutaneously or orally. Clonidine (0.2 mg/kg) was administered orally when the test compound was given subcutaneously and subcutaneously when the test compound was administered orally. Twenty minutes after the administration of clonidine, PPQ (3 mg/kg) was given intraperitoneally. Beginning five minutes after injection of PPQ, the mice were observed for writhing for a period of five minutes. The number of mice that writhed at least three times during the five minute observation period was counted. The number of mice that writhed was scored for each dose of antagonist, and the percentage reversal of clonidine-induced anti-nociception (analgesia) was calculated by dividing the number of animals writhing by the total number of test animals and multiplying the quotient by 100. The results are also expressed as an $ED_{50}$, the effective dose (in mg./kg.) in 50% of the animals to effect antagonism of clonidine-induced analgesia.

The testing results for the compounds of the invention so-obtained are given in Table 5.

TABLE 6

| Example No. | Clonidine [$^3$H] Binding % I Conc. (nM) | Rat Vas Deferens % A Conc. (nM) | Antagonism of Clonidine Analgesia % A Dose ($ED_{50}$) |
| --- | --- | --- | --- |
| 1A | $K_i = 0.92$ | $pA_2 = 8.45$ | $ED_{50} = 0.0071$ (s.c.) |
|  |  |  | $ED_{50} = 0.75$ (p.o.) |
| 1B | $K_i = 0.46$ | $pA_2 = 8.48$ | $ED_{50} = 12$ (s.c.) |
| 1C | $K_i = 0.91$ | $pA_2 = 8.91$ | $ED_{50} = 0.034$ (s.c.) |
|  |  |  | $ED_{50} = 0.098$ (p.o.) |
| 1D | 85% (1000) | $PA_2 = 6.96$ | $ED_{50} = 11.1$ (p.o.) |
| 1E | $K_i = 2.3$ | $pA_2 = 7.93$ | $ED_{50} = 0.18$ (s.c.) |
|  |  |  | $ED_{50} = 0.051$ (p.o.) |
| 1F | $K_i = 3.393$ | $pA_2 = 7.55$ | $ED_{50} = 8.8$ (p.o.) |
| 1G | $K_i = 355.4$ | 2, 34% (100) | 0% (30) (s.c.) |
|  |  | 1, 98% (500) |  |
| 1H | $K_i = 2.0$ | $pA_2 = 8.56$ | $ED_{50} = 1.5$ (p.o.) |
| 1I | $K_i = 259.9$ |  |  |
| 1J | $K_i = 1.927$ | $pA_2 = 8.76$ |  |
| 1K | $K_i = 0.77$ | $pA_2 = 8.80$ | 100% (1.0, 3.0, 10.0) (s.c.) |
|  |  |  | 70% (0.03) (s.c.) |
| 1L | $K_i = 3.5$ | $pA_2 = 8.80$ | 100% (5.5, 10.0) (s.c.) |
|  |  |  | 20% (3.0) (s.c.) |
| 1M | $K_i = 0.47$ | $pA_2 = 9.07$ | $ED_{50} = 2.6$ (p.o.) |
| 1N | $K_i = 26.0$ | $pA_2 = 7.81$ | $ED_{50}$ is $= 26.5$ (p.o.) |
| 1O | $K_i = 2.11$ | $pA_2 = 8.16$ | $ED_{50} = 1.8$ (p.o.) |
| 1P | $K_i = 53.6$ | $pA_2 = 7.59$ | $ED_{50} = 11.3$ (s.c.) |
| 1Q |  | 81% (100) |  |
|  |  | 94 (500) |  |
| 1R |  | 100% (100) | $ED_{50} = 19.8$ (p.o.) |
| 1S | $K_i = 12.3$ | $pA_2 = 8.0$ | $ED_{50} = 60.1$ (p.o.) |
| 1T | $K_i = 72.3$ | $pA_2 = 6.96$ | $ED_{50} = 41$ (p.o.) |
| 1U | $K_i = 13.8$ | $pA_2 = 8.03$ | $ED_{50} = 3.8$ (p.o.) |
| 1V | $K_i = 1.5$ (1) | $pA_2 = 8.13$ | $ED_{50} = 2.6$ (p.o.) |
| 1W | 44.6% (1000) | 4, 77% (10) |  |
|  |  | 0, 1% (1) |  |
|  |  | 2, 3% (0.1) |  |
| 1X | $K_i = 46.67$ | $pA_2 = 7.48$ | 50, 60, 50% (100, 30, 10) (s.c.) |
|  |  |  | 50, 10, 0% (100, 30, 10) (p.o.) |
| 1Y | 32.5 (1000) | 3%, 3% (100) |  |
|  |  | 5, 19% (500) |  |
|  |  | 7, 28% (1000) |  |
| 1Z | $K_i = 6.9$ | Inac. as antagonist | 0% (0-300) (p.o.) |
|  |  |  | 0, 0, 30, 70, 80% |

TABLE 6-continued

| Example No. | Clonidine [$^3$H] Binding % I Conc. (nM) | Rat Vas Deferens % A Conc. (nM) | Antagonism of Clonidine Analgesia % A Dose (ED$_{50}$) |
|---|---|---|---|
| | | but active as agonist | (10, 3, 1, 0.3, 0.1) (s.c.) |
| 1AA | 43.5 | 6, 7, 52% (100, 100, 500)$^{(d)}$ | ED$_{50}$ = 21.8 (p.o.) ED$_{50}$ = 2.6 (s.c.) 0, 10, 70% (1, 10, 30) (p.o.) |
| 1AB | K$_i$ = 13 | $^{(e)}$ | 0%, 90% (10, 30) (p.o.) |
| 1AC | K$_i$ = 25 | $^{(e)}$ | 50% (10, 30) (p.o.) |
| 1AD | | $^{(f)}$ | |
| 1AE | | $^{(g)}$ | |
| 1AF | | $^{(h)}$ | |
| 1AG | | $^{(i)}$ | |
| 2 | | $^{(j)}$ | |

$^{(d)}$Also reduced twitch height as 500 nM by 67% and 74% reversed by yohimbine
$^{(e)}$Twitch height reversed by yohimbine
$^{(f)}$20 μm gave 3.5 fold shift of clonidine
$^{(g)}$20 μm gave 15 fold shift of clonidine
$^{(h)}$10 μm gave 23.9 fold shift of clonidine
$^{(i)}$10 μm gave 3.9 fold shift of clonidine
$^{(j)}$10 μm gave 9 fold shift of clonidine

I claim:
1. A compound having the formula:

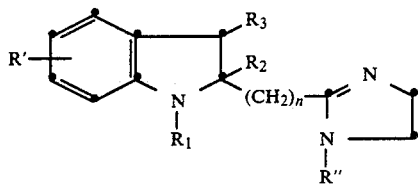

wherein:
R' is hydrogen;
R'' is hydrogen or lower-alkyl;
R$_1$ is hydrogen, lower-alkyl, lower-alkenyl, phenyl or phenyl-lower-alkyl;
R$_2$ is hydrogen or lower-alkyl;
R$_3$ is hydrogen or lower-alkyl; and
n is 0 or the integer 1;
or a pharmaceutically acceptable acid-addition salt thereof, and wherein said lower-alkyl groups in all instances contain from one to four carbon atoms.

2. A compound according to claim 1 where:
R'' is hydrogen;
R$_1$ is hydrogen, lower-alkyl, lower-alkenyl or phenyl-lower-alkyl;
n is 0
or a pharmaceutically acceptable acid-addition salt thereof.

3. A compound according to claim 2 where R$_3$ is hydrogen or a pharmaceutically acceptable acid-addition salt thereof.

4. 2-(4,5-Dihydro-1H-imidazol-2-yl)-2,3-dihydro-1-methyl-1H-indole or a pharmaceutically acceptable acid-addition salt thereof according to claim 3.

5. 2-(4,5-Dihydro-1H-imidazol-2-yl)-2,3-dihydro-1-methyl-1H-indole or a pharmaceutically acceptable acid-addition salt thereof according to claim 3.

6. 2-(4,5-Dihydro-1H-imidazol-2-yl)-2,3-dihydro-1-benzyl-1H-indole or a pharmaceutically acceptable acid-addition salt thereof according to claim 3.

7. 2-(4,5-Dihydro-1H-imidazol-2-yl)-2,3-dihydro-1,2-dimethyl-1H-indole or a pharmaceutically acceptable acid-addition salt thereof according to claim 3.

8. 2-(4,5-Dihydro-1H-imidazol-2-yl)-2,3-dihydro-1-(2-propenyl)-1H-indole or a pharmaceutically acceptable acid-addition salt thereof according to claim 3.

9. 2-(4,5-Dihydro-1H-imidazol-2-yl)-2,3-dihydro-1H-indole or a pharmaceutically acceptable acid-addition salt thereof according to claim 3.

10. 2-(4,5-Dihydro-1H-imidazol-2-yl)-2,3-dihydro-1,3-dimethyl-1H-indole or a pharmaceutically acceptable acid-addition salt thereof according to claim 2.

11. A compound having the formula:

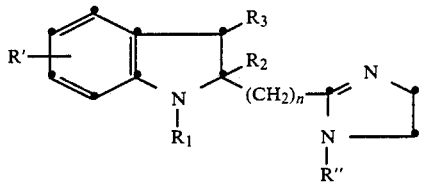

where:
R' is hydrogen, benzyl or halogen selected from chlorine or fluorine;
R'' is hydrogen or lower-alkyl;
R$_1$ is hydrogen, lower-alkyl, lower-alkenyl, lower-alkoxy-lower-alkyl, phenyl or phenyl-lower-alkyl;
R$_2$ is hydrogen, lower-alkyl, lower-alkenyl, lower-alkoxy-lower-alkyl, lower-alkylmercapto-lower-alkyl or di-lower-alkylamino-lower-alkyl;
R$_3$ is methylene; and
n is 0 or the integer 1;
or a pharmaceutically acceptable acid-addition salt thereof, and wherein said lower-alkyl, lower-alkoxy, lower-alkylmercapto and lower-alkylamino groups in all instances contain from one to four carbon atoms.

12. A compound having the formula:

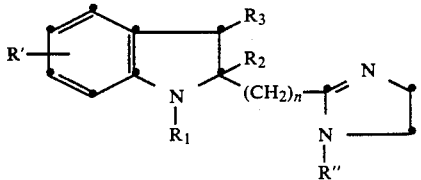

where:
R' is halogen selected from chlorine and fluorine or benzyl;
R'' is hydrogen or lower-alkyl;

$R_1$ is hydrogen, lower-alkyl, lower-alkenyl, lower-alkoxy-lower-alkyl, phenyl or phenyl-lower-alkyl;

$R_2$ is hydrogen, lower-alkyl; lower-alkenyl, lower-alkoxy-lower-alkyl, lower-alkylmercapto-lower-alkyl or di-lower-alkylamino-lower-alkyl;

$R_3$ is hydrogen or lower-alkyl; and n is 0 or the integer 1;

or a pharmaceutically acceptable acid-addition salt thereof, and wherein said lower-alkyl, lower-alkoxy, lower-alkylmercapto and lower-alkylamino groups in all instances contain from one to four carbon atoms.

13. A compound according to claim 12 where:

R' is halogen;

R" is hydrogen;

$R_1$ is lower alkyl;

$R_2$ is hydrogen;

$R_3$ is hydrogen; and n is 0;

or pharmaceutically acceptable acid-addition salt thereof.

14. 2-(4,5-Dihydro-1H-imidazol-2-yl)-5-fluoro-2,3-dihydro-1-methyl-1H-indole or a pharmaceutically acceptable acid-addition salt thereof according to claim 13.

15. A compound in the form of the racemate or an optically active isomer having the formula:

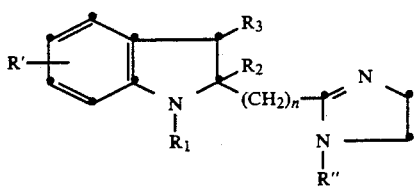

where:

R' is hydrogen;

R" is hydrogen;

$R_1$ is lower-alkyl, lower-alkenyl or phenyl-lower-alkyl;

$R_2$ is hydrogen;

$R_3$ is hydrogen; and n is 0;

or an acid-addition salt thereof.

16. A pharmaceutical composition for use as an $\alpha_2$-antagonist which comprises, as active ingredient, an effective amount of at least one indole derivative or salt as claimed in claim 15 in association with a pharmaceutically acceptable excipient.

17. A compound having one of the formulas:

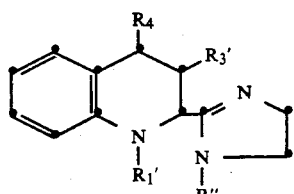

II

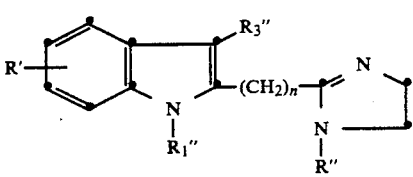

III where in the compounds of formula II;

R" is hydrogen or lower-alkyl;

$R_1'$ is hydrogen or lower-alkyl;

$R_3'$ is hydrogen or lower-alkyl; and $R_4$ is hydrogen or phenyl; and in the compounds of formula III:

R' is hydrogen, halogen selected from chlorine and fluorine or benzyl;

R" is hydrogen or lower-alkyl;

$R_1"$ is lower-alkyl;

$R_3"$ is hydrogen or lower-alkoxy; and n is 0 or the integer 1;

or a pharmaceutically-acceptable acid-addition salt thereof, and wherein said lower-alkyl and lower-alkoxy groups in all instances contain form one to four carbon atoms.

18. A compound according to claim 17 having the formula II or a pharmaceutically acceptable acid-addition salt thereof.

19. A compound accord in to claim 17 have the formula III or a pharmaceutically acceptable acid-addition salt thereof.

20. A compound according to claim 18 where:

$R_1'$ is hydrogen or lower-alkyl; and $R_3'$ and $R_4$ are hydrogen or a pharmaceutically acceptable acid-addition salt thereof.

21. 2-(4,5-Dihydro-1H-imidazol-2-yl)-1-methyl-1,2,3,4-tetrahydroquinoline or a pharmaceutically acceptable acid-addition salt thereof according to claim 20.

22. 2-(4,5-Dihydro-1H-imidazol-2-yl)-1,2,3,4-tetrahydroquinoline or a pharmaceutically acceptable acid-addition salt thereof according to claim 20.

23. 2-[(4,5-Dihydro-1H-imidazol-2-yl)methyl]-1-methyl-1H-indole or a pharmaceutically acceptable acid-addition salt thereof according to claim 19.

24. A composition for treating depressed states in warm blooded animals which comprises an antidepressantly effective amount of a compound according to claim 1 together with one or more pharmaceutically acceptable excipients.

25. A composition for treating depressed states in warm blooded animals which comprises an antidepressantly effective amount of a compound according to claim 11 together with one or more pharmaceutically acceptable excipients.

26. A composition for treating depressed states in warm blooded animals which comprises an antidepressantly effective amount of a compound according to claim 12 with one or more pharmaceutically acceptable excipients.

27. A composition according to claim 26 containing 2-(4,5-dihydro-1H-imidazol-2-yl)-5-fluoro-2,3-dihydro-1-methyl-1H-indole or a pharmaceutically acceptable acid-addition salt thereof as the antidepressant agent.

28. A composition for treating depressed states in warm blooded animals which comprises an antidepressantly effective amount of a compound according to claim 17 together with one or more pharmaceutically acceptable excipients.

29. A composition for treating depressed states in warm blooded animals which comprises an antidepressantly effective amount of a compound of formula II according to claim 17.

30. A composition for treating depressed states in warm blooded animals which comprises an antidepressantly effective amount of a compound of formula III according to claim 17.

31. A method for treating depressed states in warm blooded animals which comprises administering an antidepressantly effective amount of a composition according to claim 1.

32. A method for treating depressed states in warm blooded animals which comprises administering an antidepressantly effective amount of a composition according to claim 11.

33. A method for treating depressed states in warm blooded animals which comprises administering an antidepressantly effective amount of a composition according to claim 12.

34. A method according to claim 33 wherein the antidepressant agent is 2-(4,5-dihydro-1H-imidazol-2-yl)-5-fluoro-2,3-dihydro-1-methyl-1H-indole or a pharmaceutically acceptable acid-addition salt thereof.

35. A method for treating depressed states in warm blooded animals which comprises administering an antidepressantly effective amount of a composition according to claim 17.

36. A method for treating depressed states in warm blooded animals which comprises administering antidepressantly effective amount of a compound of formula II according to claim 17.

37. A method for treating depressed states in warm blooded animals which comprises administering an antidepressantly effective amount of a compound of formula III according to claim 17.

* * * * *

UNITED STATES PATENT AND TRADEMARK OFFICE
CERTIFICATE OF CORRECTION

PATENT NO. : 5,017,584
DATED : May 21, 1991
INVENTOR(S) : Dennis J. Hlasta

It is certified that error appears in the above-identified patent and that said Letters Patent is hereby corrected as shown below:

Column 4, line 46, after "temperature" insert -- in the range from 50 to about 150°C in the presence --.

Column 23, line 58, Claim 5, "methyl-1H-" should read -- ethyl-1H- --.

Column 25, line 19, Claim 13, "or" should read -- or a --.

Column 26, line 1, Claim 17, "II;" should read -- II: --;
line 15, Claim 17, "form" should read -- from --;
line 20, Claim 19, "accord in" should read -- according --; and "have" should read -- having --.

Column 28, line 9, Claim 36, "an-" should read -- an an- --.

Signed and Sealed this

Third Day of August, 1993

Attest:

MICHAEL K. KIRK

*Attesting Officer*     Acting Commissioner of Patents and Trademarks